United States Patent [19]

Susic

[11] Patent Number: 5,084,003

[45] Date of Patent: Jan. 28, 1992

[54] MAGNETIC MASSAGE THERAPY DEVICE

[76] Inventor: Dragan Susic, Milorado Pantica 33 b, Beograd-Ostruznica, Yugoslavia

[21] Appl. No.: 452,734

[22] Filed: Dec. 21, 1989

[30] Foreign Application Priority Data

Nov. 24, 1989 [DE] Fed. Rep. of Germany ....... 3938920

[51] Int. Cl.⁵ ............................................. A61N 2/00
[52] U.S. Cl. ...................................... 600/13; 600/15
[58] Field of Search ................. 600/9, 13–15; 128/32

[56] References Cited

U.S. PATENT DOCUMENTS 2,597,601  5/1952  Sherman ............................. 600/15

FOREIGN PATENT DOCUMENTS

3246128  6/1983  Fed. Rep. of Germany ........ 600/13
8400305  2/1984  PCT Int'l Appl. ..................... 600/15
3345    9/1875  United Kingdom .................. 600/15

*Primary Examiner*—Ruth S. Smith
*Attorney, Agent, or Firm*—Browdy and Neimark

[57] ABSTRACT

A massage device having a low-frequency voltage pulse generator (IG), which supplies an electromagnetic field coil (MZ), inside of which a human or animal body is placed, on the surface of which a magnet cover or magnet apron (MS) is located inside the field coil (MZ) and which is comprised of small permanent magnet magnetic plates (PM) which are flexibly connected with each other, so that these small magnetic plates (PM) exert a massaging effect on the surface of the body, because they are excited by means of the low-frequency electromagnetic field into pivoting oscillations. The massage effect stimulates the flow of blood and draining of lymphatic fluid and increases the effect of the electromagnetic low-frequency treatment.

17 Claims, 8 Drawing Sheets

Fig.10

MAGNETIC MASSAGE THERAPY DEVICE

BACKGROUND OF THE INVENTION

1. Field of the Invention

The invention relates to a treatment device for a human or animal body or parts thereof with a low-frequency, electro-magnetic field coil surrounding it.

2. Prior Art

The device according to the invention is very useful in the field of physical therapy and for the rehabilitation of people. This novelty provides an improvement of the known method for use of a low-frequency electromagnetic field, called low-frequency therapy.

It is an object of the invention to increase the effectiveness of low-frequency therapy and to broaden the scope of its use.

This object is attained by means of the use of low-frequency therapy together with small magnetic plates disposed on the subject of the treatment.

Advantageous embodiments are recited in the dependent claims.

Advantageously, the small magnetic plates are comprised of permanent magnet material and are disposed at a distance from each other in a cover or bandage and maintained therein pivotable in respect to each other, so that they can easily be disposed and maintained on the subject of the treatment, but perform pivoting movements in the electromagnetic field because of the interaction of the magnetic fields which, supplementing the therapeutic effect of the magnetic fields, advantageously provide a therapeutic massage effect.

In an advantageous design of the total device, the coil arrangement used for generating the low-frequency field which encloses the subject of the treatment and the permanent magnet arrangement, i.e. the magnet support cover or bandage, is comprised of flexible coils, which simplifies the transport and handling of the arrangement.

An advantageous design of the device is supplied by a low-frequency pulse generator with a pre-determined frequency and amplitude.

Medical scientific tests using the novel device have shown its advantageous effects, compared with previously known devices. Tests on people and animals have shown a considerably higher degree of effectiveness in the treatment of post-traumatic conditions compared with only the use of the previously known low-frequency therapy. The tests were performed with an electro-magnetic low-frequency pulse emitter of two designs, namely: firstly by generating pulses of a frequency pre-determined in a range between 0.5 to 30 Hz, the pulses of which comprised waves of sinusoidal or semi-sinusoidal shape having a base frequency of 60 Hz, and secondly by use of rectangular pulses with a predetermined frequency in a range between 1 to 1,000 Hz. The arrangement of the field coils was of a known form in these tests.

Part of the novel device is a specially designed magnetic cover. It consists of a plurality of small permanent magnets, which are oriented in a particular way and are separated from each other and arranged in respect to each other in a particular manner. This causes a very subtle vibration of the rigid, movably disposed magnets in an electromagnetic low-frequency field, which causes micro-massage of the vessels covered by it. The primary effect of this micro-massage is the widening of the small blood vessels and the improvement of the flow in the lymphatic system, i.e. improved draining of the lymphatic system. Additionally, this type of massage results in a recuperative effect on the affected skeletal musculature. These effects are added on top of the known positive effects of magnetic and low-frequency therapy and result in a synergistic effect. The effect of the massage already becomes noticeable after a few minutes and the relaxation and increased blood flow caused by it make it possible that the low-frequency therapy, the effects of which are only noticeable over extended periods of time, can operate more efficiently.

It has been shown in an advantageous manner that the use of bandages equipped with permanent magnets, which are used as compresses for limbs with injuries, for example with strains or lacerated muscles, and which are excited to vibratory massage in the low-frequency field, avoids the disadvantageous congestion of blood or lymphatic fluid, common with bandages, behind the bandage in the areas of the extremities far from the heart, so that quicker healing of the injury, free of pain and the need for follow-up treatment, was accomplished.

In a first embodiment, in particular suitable for the human body, the field coil arrangement is disposed on a bed, with coil guides extending in the longitudinal direction. The coil guides advantageously extend above and below the surface of the bed and of the body to be treated. The upper coil half is advantageously fastened in a pivotable manner, thus making possible unrestricted lying down and rising. The bed has rollers, preferably blockable rollers.

A second embodiment of the invention has one, or preferably a plurality of coils surrounding the body, which are slidably disposed and supported next to each other on a mobile bed and the coil axes of which are oriented in the longitudinal direction of the bed.

A further advantageous embodiment of the coil arrangement consists of supporting them on a mobile platform. The inner dimensions of the coil are large enough that it can surround the body of an animal and it extends below the platform, laterally and above the body of the animal and with its axis in the direction of the body of the animal. The coil extends far enough upward so that the animal can enter it and walk through it without difficulties. The platform is provided with a trailer hitch and the device can be used as transport for animals in an advantageous manner.

A further advantageous embodiment of the invention, usable with various arrangements of the coils, is the result of burying small permanent magnet plates in a plastic sheath which is supported on a plastic frame, freely movable and pivotable within limits, by means of a loose nut-spring connection on opposite sides. These button-like frames equipped with small magnetic plates can be cast in a plastic body or fixed on a cover.

In a special embodiment, the plastic body is in the form of an oral insert, the movably supported small magnetic plates contacting the bases of the teeth on both sides and in this way are used for massaging them.

A further advantageous embodiment relates to the low-frequency current generator encompassing a plurality of controllable pulse generators which are individually connected with the several magnetic coils disposed along the body and which are controlled by a control device in such a way, that they impart the pulses to the coils in a pre-determined phase correlation and predetermined frequency. By means of this type of phase-shifted excitation, i.e. advancing in waves from the feet towards the head or towards the heart, the small magnetic plates excited in this manner provide an advantageous peristaltic draining effect. The body is covered to a large degree by a cover embedded with small magnetic plates.

Expanded and new areas of employment of the magnetic massage therapy result from the above special embodiments. Treatment and regenerative stimulation of the tissues of the oral cavity and of the gums becomes advantageously possible by means of the oral insert in connection with various diseases, in particular with periodontosis, because a major cause of this disease is a reduced micro-circulation in the tissues, which is counteracted by means of this treatment. Treatment is very simple, because the patient merely needs to insert the denture-like oral insert and then lie for some time on the bed with the field coil arrangement.

A further advantageous embodiment of the button-like magnet holders consists in disposing them on certain acupressure points, depending on the particular indication, and then to expose the body to the stimulating alternating magnetic field.

Treatment of animals is in particular applicable to horses prior to or following stresses caused by sports events. The disposition of the magnetic field coils in the transport vehicle makes it possible to easily treat the animals immediately prior to or after the sports event at the location of the event. It is also possible to provide treatment without a loss of time during the movement to or from the event. The movable small magnetic plates are embedded in suitable covers or leggings.

In a preferred manner the control device for the pulse generators has two different programs. One works in the manner of a progressive phase shift of the pulses in such a way that the various field coils generate a sort of peristaltic wave in the small magnetic plates. Another type is the provision of different frequencies to the field coils distributed over the body, where the frequencies are varied at intervals or slowly and continuously, so that the interferences of the different frequencies act on the treated body.

BRIEF DESCRIPTION OF THE DRAWINGS

Advantageous embodiments and applications are shown in FIGS. 1 to 26.

FIG. 13 is a lateral view, partially cut, of a first field coil arrangement for a bed;

FIG. 14 is a schematic front view in a first pivot position according to FIG. 13;

FIG. 15 is a front view in a second pivot position according to FIG. 13;

FIG. 16 is a lateral view of a treatment device for an

FIG. 17 is a back view of a treatment device for an animal;

DETAILED DESCRIPTION OF THE PREFERRED EMBODIMENT

Figure 1:
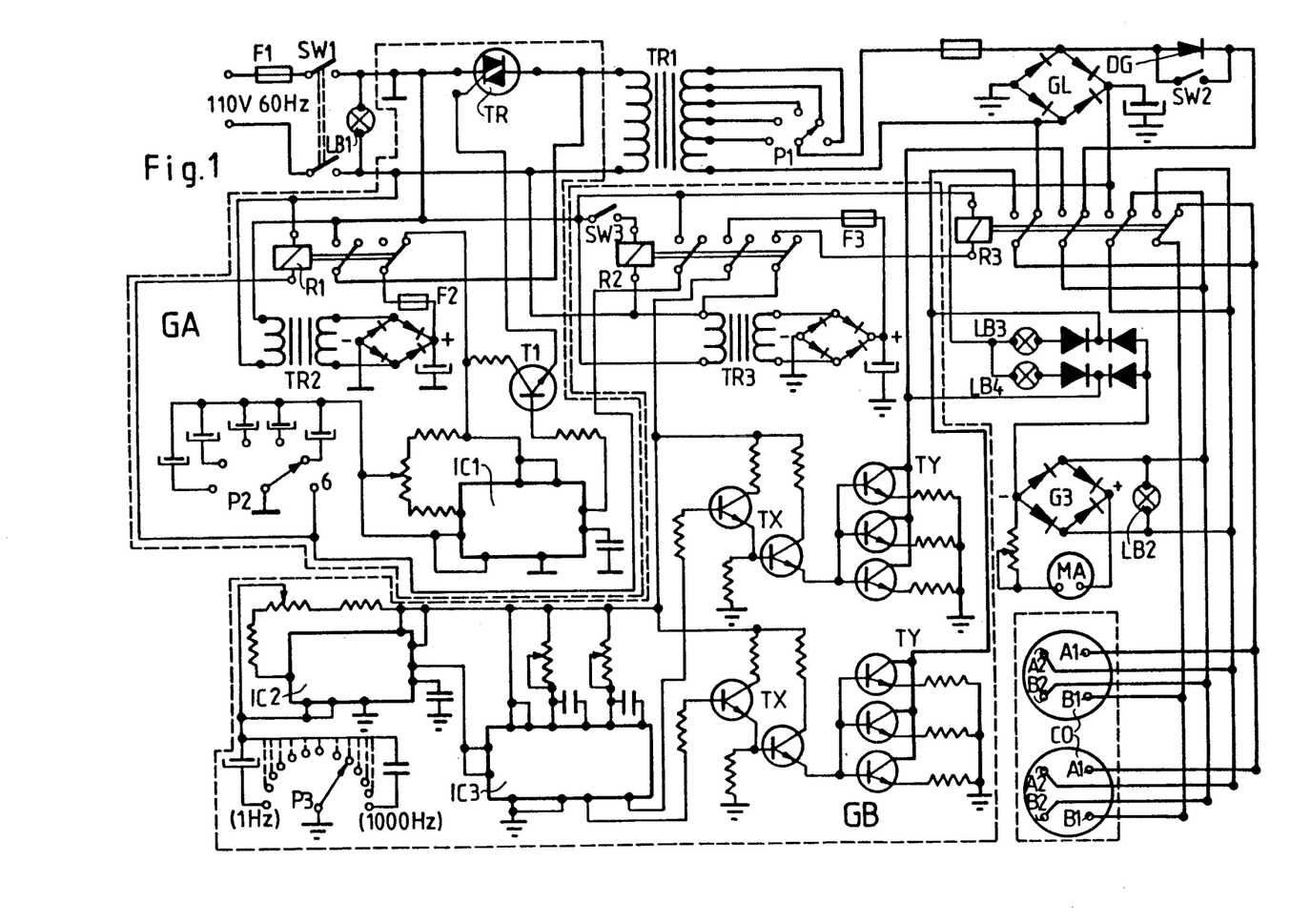
FIG. 1 is a circuit diagram of a pulse generator of the device.

FIG. 1 is a wiring diagram of the electrical pulse generator, which is supplied by the A/C net (60 Hz, 10 V) when the switch (SW1) is turned on. Protection is provided by the fuse (F1) and operation is indicated by the indicator lamp (LB1). The operational mode switch (SW3) is used to switch to an operational mode which works with the aid of the net frequency, where, if it is in the "off" position, signals of a pulse frequency between 0.5 and 30 Hz are generated and signals having a sinusoidal or semisinusoidal path are created. The first oscillator (IC1) is supplied with current via a net transformer (TR2), a net rectifier, a second fuse (F2) and a relay contact of a first relay (R1). The integrated first oscillator (IC1) then generates a predetermined frequency between 0.5 to 30 Hz, dependent on the capacitors switched in by means of a frequency range switch (P2). The transistor (T1) amplifies the oscillator signal, its signal controlling a triac (TR) which supplies the alternate voltage input signal to a signal transformer (TR1) in a correspondingly clocked manner. The secondary windings of the latter are selected by the output selector switch (P1), and the selected signal is supplied to the output via a switch (SW2), depending on its position, either directly or via a half-wave rectifier (DG). Accordingly, either full- or half-wave output signals are being periodically generated in accordance with the oscillator frequency. After being rectified and filtered, the output signal, which is output at the plug connectors (CO), is supplied to a level meter (MA), the scale of which is advantageously calibrated corresponding to the magnetic field strength of the field coil. A control light (LB2) indicates the operational state. If the range switch (P2) is in a particular end position (6), the first relay (R1) is switched over, because of which the first oscillator (IC1) is switched off and the net frequency is supplied directly to the transformer (TR1) and is emitted, according to the switch position, either directly or as half-waves.

If the operational mode switch (SW3) is in the "on" position, the second generator (GB), shown in an area surrounded by dashed lines, is operational in place of the already described first generator (GA) in the other area surrounded by dashed lines. The second generator (GB) supplies rectangular pulses of a frequency between 1 to 1,000 Hz, depending on the setting. Three relays (R1 to R3) are then switched on. The second integrated oscillator (IC2) is supplied by a transformer (TR3) via a rectifier and a fuse (F3). The second oscillator (IC2) is set at a range between 1 and 1,000 Hz by the corresponding capacitor connected by means of the selector switch (P3). The oscillator signal is supplied to a monostable pulse generator (IC3) which emits complementary rectangular pulses corresponding to the frequency, which are amplified in Darlington transistor pairs (TX), the output signals of which are supplied to two electronic switch or thyristor groups (TY) of parallel high-output thyristors. Supply with DC voltage of these thyristors (TY) is provided via a rectifier (G), which is switched downstream of the output selector switch (P1). Switched in downstream of each of the two thyristor groups (TY) are operational mode indicators (LB3, LB4), the outputs of which are supplied to contacts (A1, A2; B1, B2) of the plug connectors (CO) into which the cable for the field coils is to be plugged.

Figures 2, 2A:
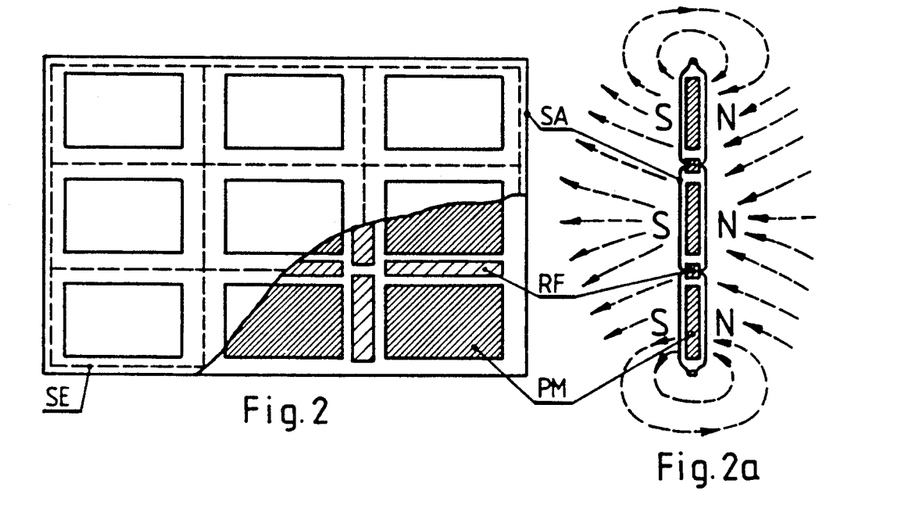
FIG. 2 is a top view of a section of the arrangement of the magnets in a cover.
FIG. 2a is a cross-section according to FIG. 2.

FIGS. 2 and 2a show a section of a top view and a cross-section of a magnet cover. It is comprised of small permanent magnets (PM), which may be of various sizes and shapes. The number of magnets depends on the size of the cover. They are maintained next to each other inside a fabric sheath (SA), for example of linen, with an elastic filler material (RF), for example of rubber, being placed between them and sewn to the fabric sheath (SA) along the edges of the magnets, as shown by the seam (SE) indicated by dashed lines. This design of the magnet cover has an egg crate structure. All magnets are oriented in the same direction, as shown in FIG. 2a, and their magnetic axes lie vertically to the extent of the cover.

Figure 3:
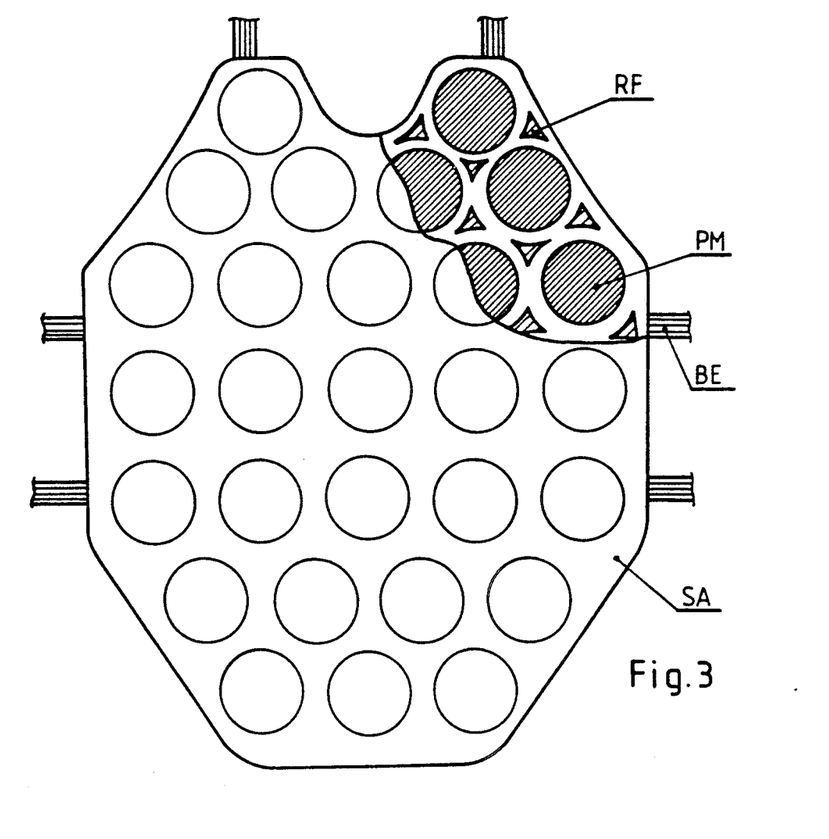
FIG. 3 is an apron-like cover with a further arrangement of magnets.

FIG. 3 shows an alternate arrangement of the magnets (PM) in the shape of a magnet apron filled with a multitude of small round magnet plates, around which a fabric sheath (SA) has been sewn. The spaces between them are filled with rubber material (RF). Edges (BE) are laterally fixed on the apron and are used to fasten it on the body of a patient. The magnet cover or magnet apron generate the micro-massage in the alternating electromagnetic field. If the latter is switched on, the permanent magnets oscillate because of the alternating magneto-mechanical forces generated and effect a light massage of the covered part of the body. This creates a salubrious effect on living tissue, for example improved micro-circulation and release from pain.

Figures 4, 4A, 5:
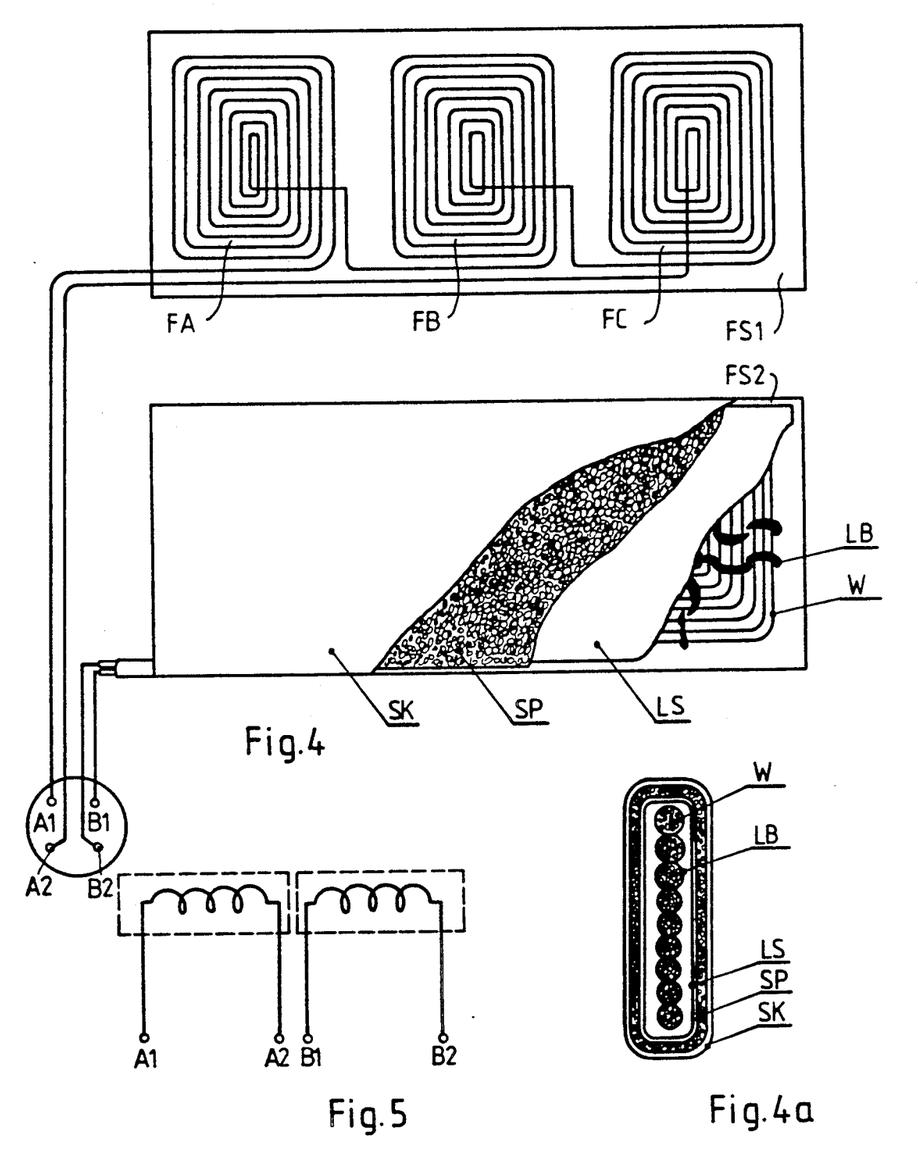
FIG. 4 is a partially cut, partially schematic view of a field coil arrangement.
FIG. 4a is a cross-section according to FIG. 4.
FIG. 5 is an electrical circuit of the field coil arrangement according to FIG. 4.

FIG. 4 shows a first, flat, flexible field coil arrangement of the device which can be produced in different sizes and is composed of a plurality of adjacently located conductor bundle sections (FA, FB, FC), each designed as rectangular spirals. A total coil arrangement is preferably formed from two separate field coil arrangements (FS1, FS2).

FIG. 4a is a cross-section and FIG. 4 is a partially cut area of the field coil arrangement. The flexible, insulated conductor bundles (W) forming the coil sections are connected with each other by a sheath (LB) and are maintained next to each other so that they form flat, rectangular spirals. The three coil sections are switched in series. They are enclosed between a fabric cover (LS) on each side and a thin layer of plastic foam (SP) and a plastic cover (SK) are advantageously placed around the fabric cover (LS).

As shown schematically in FIG. 5, the two coil arrangements (FS1, FS2) are supplied with current and disposed on top of each other or adjacent to each other in such a way that their magnetic fields are addingly superimposed on each other. The connections (A1, A2; B1, B2) are made to the plug connector (CO), FIG. 1.

Figures 6, 6A:
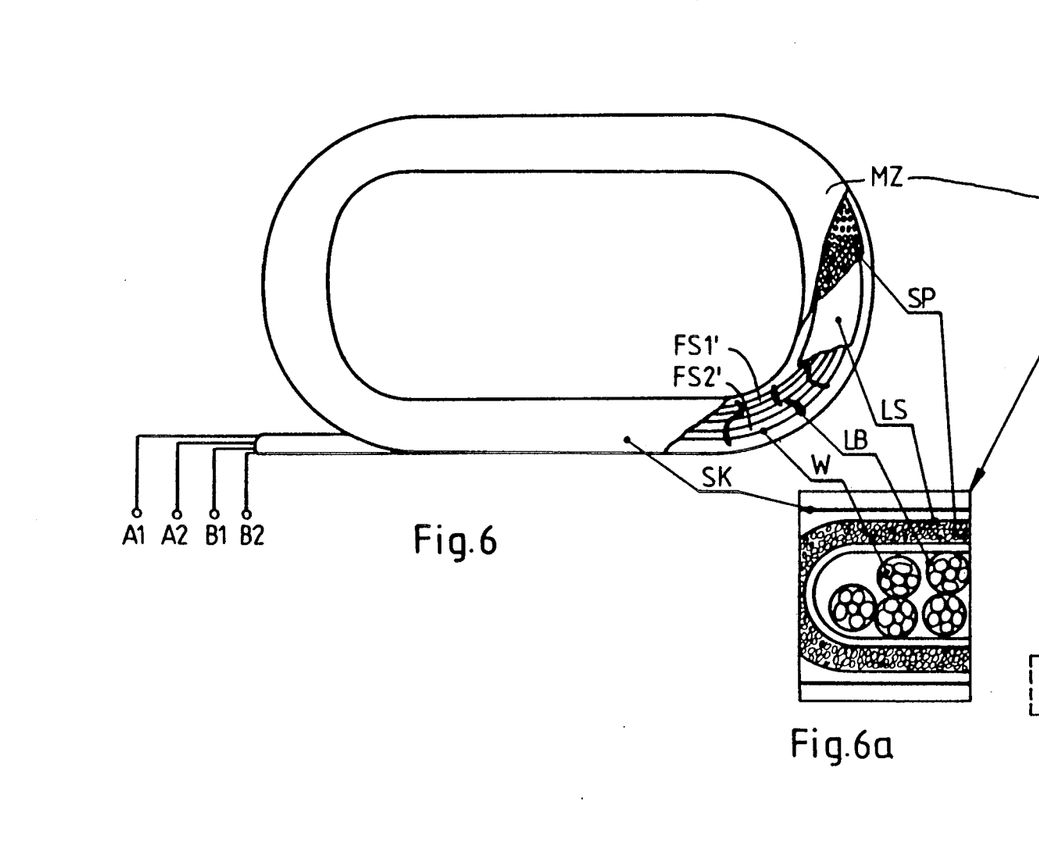
FIG. 6 is a further field coil arrangement.
FIG. 6a is a cross-section according to FIG. 6 in the form of an enlarged section.
Figure 6B:
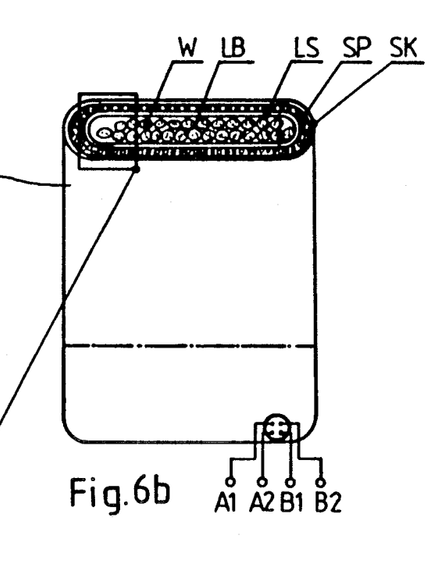
FIG. 6b is a cross-section according to FIG. 6.

FIG. 6 shows a hollow-cylindrical design of the field coil, where the two coil arrangements (FS1', FS2') made from flex cable (W) are placed directly on top of each other. The interior structure can be seen from the partially cut view, from the cross-section in FIG. 6b and the magnified cross-section in FIG. 6a. The cables (W) are provided with a sheathing (LB), for example of a ribbon of linen, which imparts to the coil its hollow-cylindrical or hollow-flat-cylindrical shape and its flexibility. The entire cylindrical coil is surrounded by a fabric sheath (LS), then a layer of plastic foam or sponge material (SP) and a cover (SK) of plastic or of a natural material. The flexible design of the coil (MZ) is very practical as far as handling and transportation are concerned, because its shape can be adapted to the requirements of each individual case.

Figure 7:
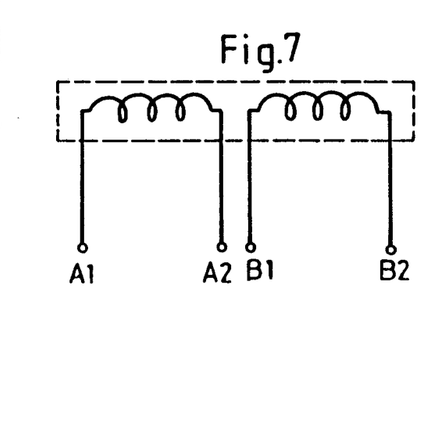
FIG. 7 is an electrical circuit of the field coil arrangement according to FIG. 6.

FIG. 7 shows the electrical connecting arrangement of the plug connectors (A1, A2; B1, B2) and the additive rectified field position.

Figure 8:
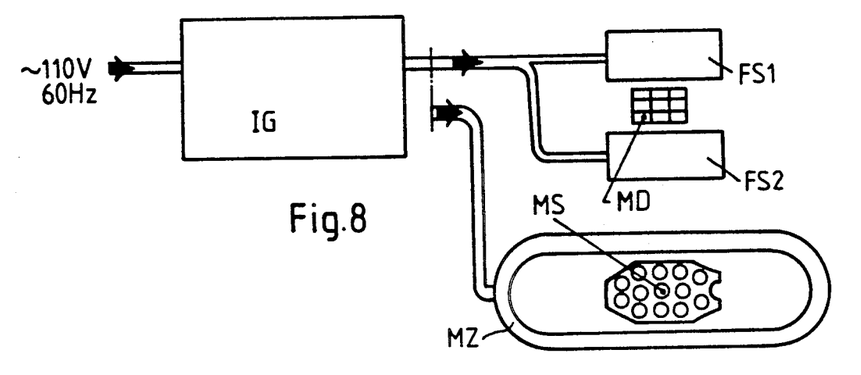
FIG. 8 is a block diagram of the total arrangement.

FIG. 8 shows a combination of the pulse generator (IG) with the selectively connectable field coil arrangements (FS1, FS2; MZ) and the magnet cover (MD) or the magnet apron (MS) in a purely schematic way.

Figures 9, 11, 12:
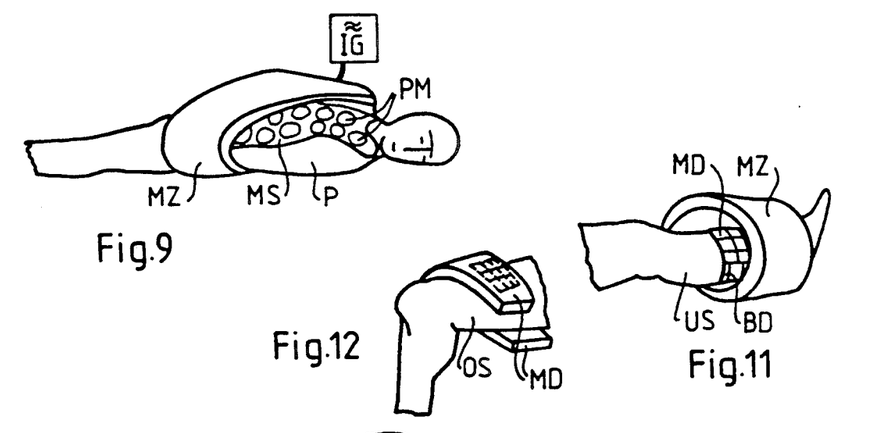
FIGS. 9 to 12 ar different arrangements of the device on a patient.

FIG. 9 shows the arrangement of a magnet apron (MS) with permanent magnets (PM) on a patient (P) and the flexible field coil arrangement (MZ) surrounding a patient (P) in the chest area and connected to the pulse generator (IG).

Figure 10:
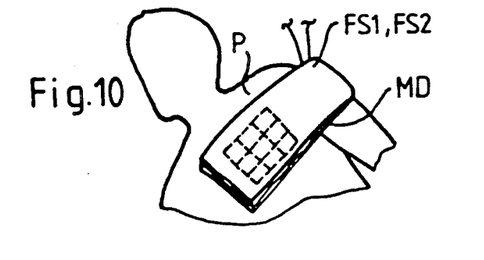

FIG. 10 shows a patient (P) during treatment of the shoulder. The magnetic coil is provided by the flexible arrangements (FS1, FS2) placed on the magnet cover (MD).

FIG. 11 shows the arrangement of a bandage (BD) with a magnet cover (MD) on the calf (US) and the surrounding cylindrical coil (MZ).

FIG. 12 shows the loose arrangement of a magnet cover (MD) on the thigh (OS); the field coil is not shown.

FIGS. 9 to 12 are merely examples of use and embodiment. Adaptation to particular modes of use and to the bodies of animals is possible for one skilled in the art. In place of the flexible coils, which are particularly pleasant in their use, it is also possible to use rigid coils. The coils as well as the magnets can also be inserted into articles of clothing. The permanent magnets used for the massage cover or massage apron can also be replaced by electromagnets, rigid per se but flexible in regard to each other, consisting of coils, through which direct current flows; however, these then will require a current supply.

A further embodiment of the permanent magnet cover or apron is the result of its being formed by a plate of magnetized magnetic rubber stamped in grids. If required, it can be provided with a fabric and/or flexible cover. The size of the small magnetic plates in respect to the length of their edges or their diameter has been found to be advantageous if in the range of 0.5 to 5 cm. The pivotal movement of the small plates in the low-frequency field of the cylindrical coil, the field of which is at right angles to the magnetization of the small plates, or the axial movement of the small plates when their fields are directed parallel to the low-frequency field of the flexible coil arrangement, together with the directionally oriented walls of the blood and lymphatic vessel, acts like a hose pump in the manner of a peristaltic movement, increasing the circulation of the blood and draining, because of which advantageous results were found in the area of applications regarding the preparation for and cooling down after physical exercises.

Figures 13, 14, 15, 16, 17:
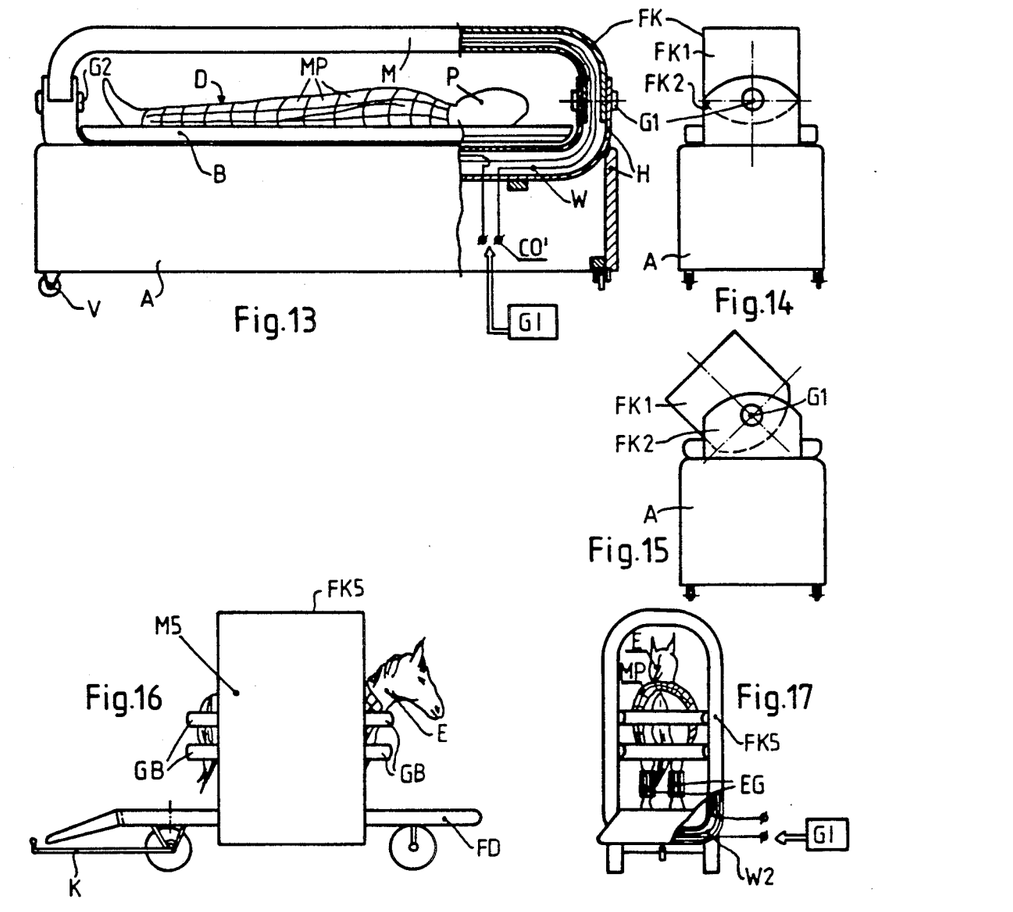

FIG. 13 shows a bed (A), movable on rollers (V), on the head and foot of which a field coil support (H) for the field coil (M) is disposed, the winding (W) of which extends through the bed (A) and above the space for the patient in a channel (FK). This channel (FK) is divided into an upper and lower channel section (FK1, FK2) and has at the head and the foot one articulated joint (G1, G2) each, through which the winding (W) flexibly extends. The winding (W) is connected to a pulse generator (GI) by means of removable connections (CO').

During treatment, a patient (P) is placed on a soft pad (B), which is preferably equipped with movable small magnetic plates. Additionally, the patient (P) is covered by a cover (D) having small magnetic plates (MP). In the position of treatment, the coil (M) is pivoted above the patient (P), as shown in the front view in FIG. 14. The coil channel (FK1) of the coil (M) extends crosswise over the patient. The channel ends are closed, in the shape of sectors of a circle, in the area of the joint (G1) and overlap, so that the winding is completely encapsuled.

FIG. 15 shows the lower and the upper channel section (FK1, FK2) pivoted away from each other around the joint (G1). In this position a patient is freely able to sit up on the bed (A) or to lie down, or to leave the bed.

Figure 18:
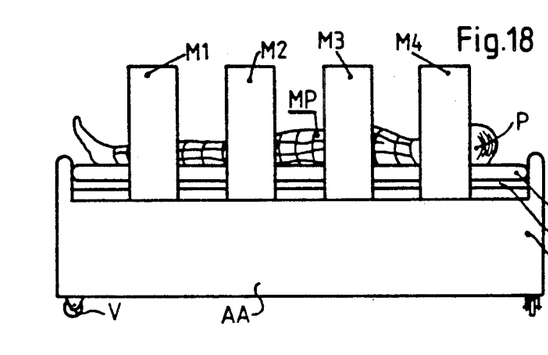
FIG. 18 is a lateral view of a second field coil arrangement for a bed.

FIG. 18 shows another design of the bed. The bed (AA) is movable on rollers (V). A pallet (C) with a pad (B), on which the patient (P) rests, extends between the head and the foot. Field coils (M1, M2, M3, M4) are coaxially disposed in the frame of the bed in such a way that they enclose the space where the patient lies and that their field axes extend in the direction of the axis of the body of a patient (P). The total length of the field coils (M1 to M4) is considerably less than the length of the bed (AA). The field coils (M1, M4) are disposed axially movable on the bed frame, so that they can be pushed together to enable the patient (P) to get up or lie down and do not constitute an obstacle.

Figure 19:
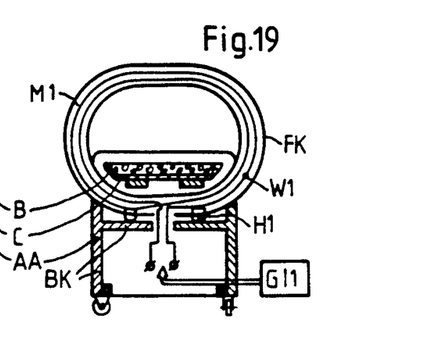
FIG. 19 is a cross-section through the arrangement of FIG. 18.

FIG. 19 is a sectional view of the bed frame (BK) of the bed (AA), with a field coil (MI) moving thereon on rollers (HI), the winding (W1) of which is protectively contained in a channel (FK). The pad (B) with the movably inserted small magnetic plates is disposed in the coil (M1, together with the pallet (C). The winding (W1) is clamped to the generator (GI1) by means of flexible connecting cables, and the other windings are also connected with it.

FIG. 16 shows a mobile platform (FD) with a trailer hitch (K) and the tongue. The field coil (M5) is disposed on the platform (FD) in such a way, that a horse (E) can enter it and walk through it. The coil (M5) is enclosed by a protective channel. Hoop gates (GB) are provided on the entry and exit of the field coil (M5), so that an animal (E) to be treated can be kept in place.

In FIG. 17 the animal treatment device is shown in front view. The coil channel (FK5) is shown partially cut away, so that the schematically indicated winding (W2) is visible, the connectors of which lead to the generator (GI). The horse (E) to be treated has a cover with small magnetic plates (MP) and leggings (EG) with movable magnets.

The entire treatment device can also be enclosed by a housing; however, use of metal parts must be avoided to the extent possible in the area of the alternating electrical field. For other types of animals, the size of the device should be adapted to their size.

Figure 20:
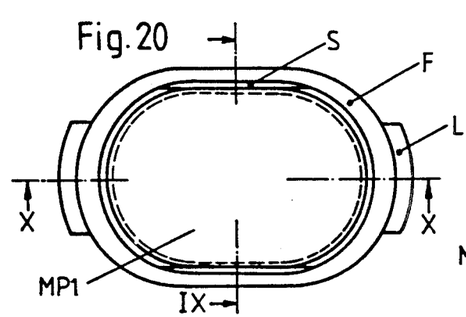
FIG. 20 is an enlarged top view of a holder for a small magnetic plate.

FIG. 20 shows an enlarged top view of the design of a small magnetic plate (MP1), which is maintained movable and pivotable by a small amount of distance and angle around the play (S) in a button-like frame (F). The frame (F) has laterally extending fastening straps (L).

Figure 21:
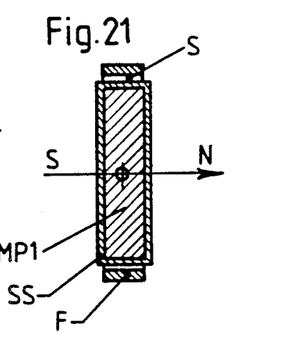
FIG. 21 is a section along IX—IX of FIG. 20.
Figure 22:
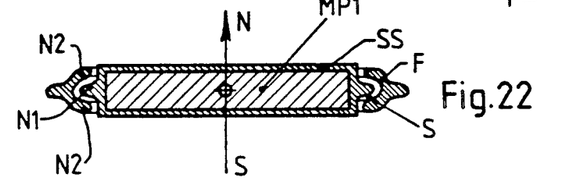
FIG. 22 is a section along X—X of FIG. 20.

As shown by the longitudinal and cross-sections in FIGS. 21 and 22, the small magnetic plate (MP1) is covered with a protective layer (SS), which has projections (N1) at opposite sides, which are maintained with play (S) in a groove (N2) of the frame (F).

Play (S) is also provided on the other sides towards the frame (F), as shown in FIGS. 20 and 21, so that the small magnetic plate can move if charged by an exterior magnetic field. Preferably the permanent magnet field (S→N) is oriented in the direction of the shortest axis of the small magnetic plate (MP1). The plastic sheathing (SS) of the small plate (MP1) allows simple cleaning and sterilization of the magnetic device. The frame (F) can be sewn or riveted by its straps (L) on a cover or can be cast in plastic.

Figure 23:
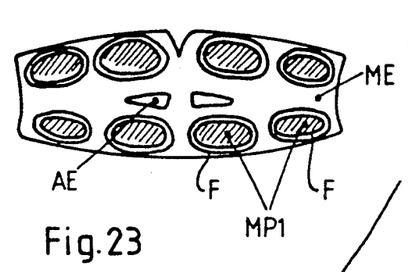
FIG. 23 is a frontal view of an oral insert.

FIG. 23 shows the small magnetic plates (MP1) with their surrounding frames (F) embedded in a denture-like oral insert (ME) preferably composed of plastic or a rubber material. Openings for breathing (AE) are disposed in the central area of the insert. The small magnetic plates (MP1) are distributed over the surface of the insert.

Figure 24:
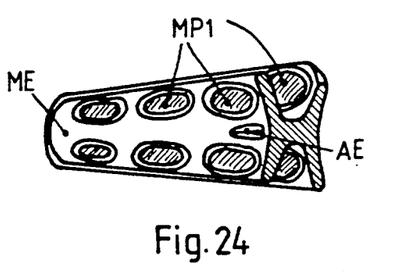
FIG. 24 is an interior view of an oral insert, cut in the center.
Figure 25:
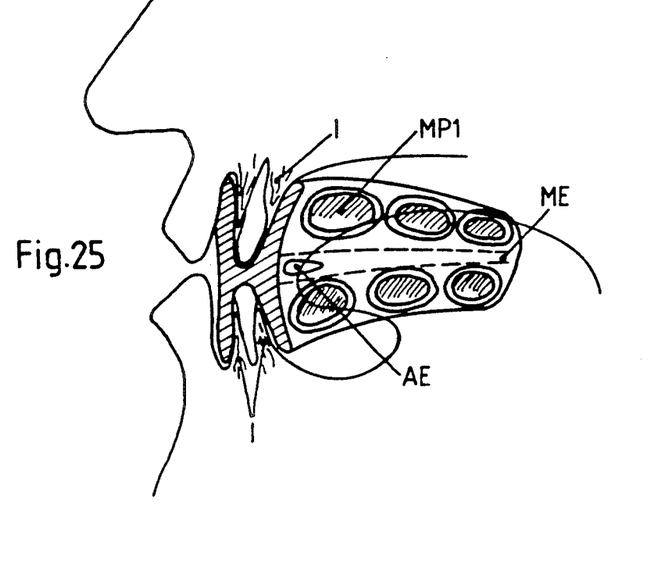
FIG. 25 is an interior view of an oral insert, cut in the center, in the position of application.

FIGS. 24 and 25 show an interior view and a cross-section of the oral insert (ME). The cross-section is approximately in the shape of a letter H, so that its legs extend at the top and bottom on both sides of the bed of the teeth. Preferably the material of the oral insert (ME) is ductile so that it adapts to the respective shape of the jaw when inserted and during the subsequent biting down and lies flat against the gums (I). In this way only an assortment of a few oral inserts of different sizes is required for a number of patients. However, it is also possible to shape a suitable oral insert from a model of the jaw of a patient.

By being in the shape of a strip or U-shaped, the oral insert can also be designed for only the inside or the outside of the jaw or only covering the upper or lower jaw.

Figure 26:
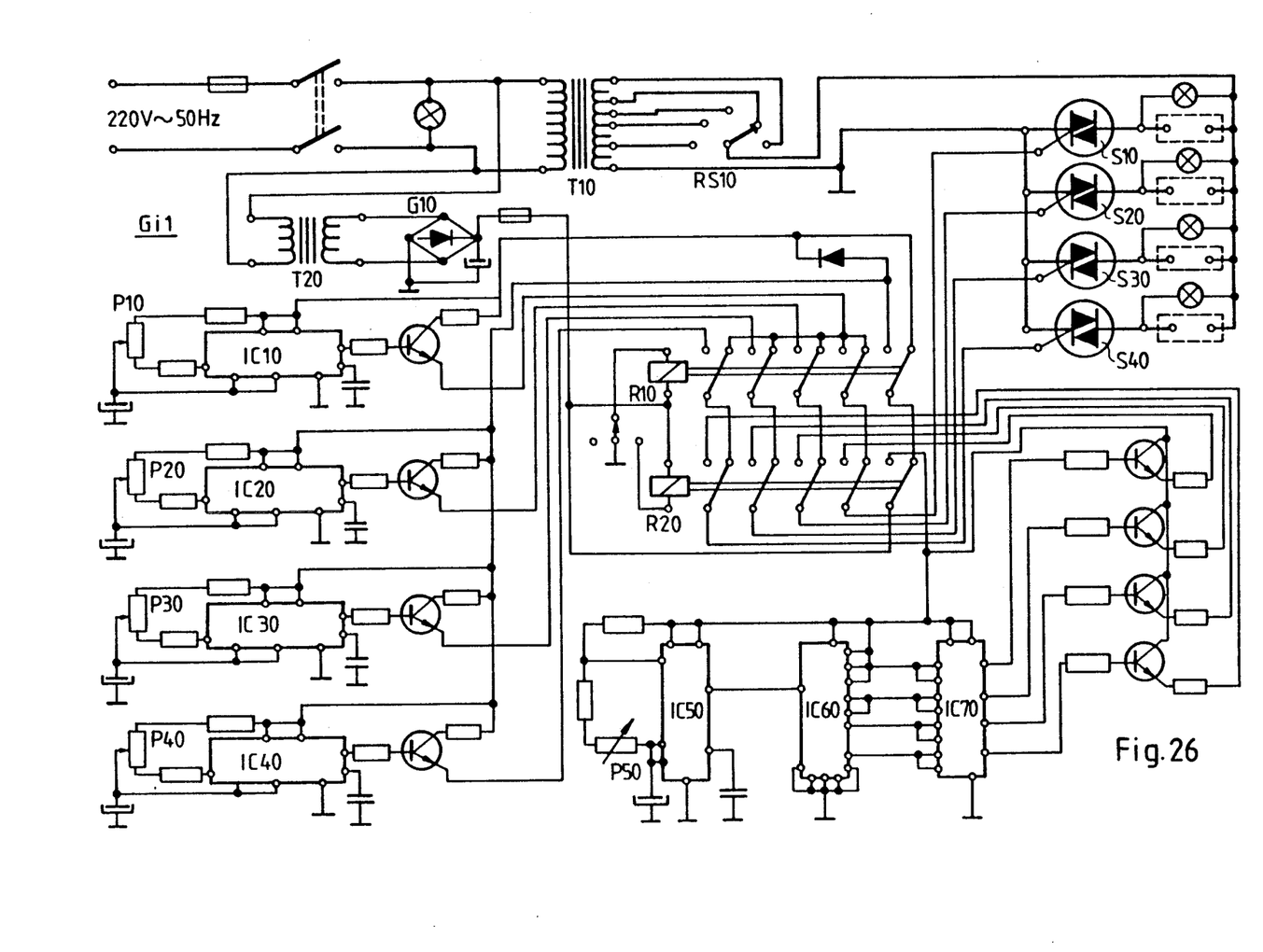
FIG. 26 is a circuit diagram of a multi-channel generator.

FIG. 26 shows an advantageous and very simple and universally usable circuit of a pulse generator (Gil) having a plurality of controllable triac switches (S10 to S40), which on the output side are connected with the clamps for the coil connections and which are supplied with alternating voltage of the frequency of the net by a step transformer (T10) via a step switch (RS10).

The triac switches (S10 to S40) are controlled either by individual pulse generators (IC10 to IC40), the frequency of which can preferably be set by means of associated potentiometers (P10 to P40), or by means of a pulse sequence circuit (IC60, IC70), the pulse sequence frequency of which is set by an oscillator (IC50) which can be set to a desired frequency by means of a potentiometer (P50). Selection of the two types of control is determined by the position of a multi-pole change-over switch (R20).

An additional multi-pole change-over switch (R10) makes possible the parallel control of all triac switches by on of the pulse generators (IC10); this switch position is shown. The various control circuits (IC10 to IC70) are connected as needed with a power supply device (T20, G10) by means of auxiliary contacts of the multi-pole switches (R10, R20). This fairly simple control device satisfies the normal therapeutic requirements. However, it can also be changed into a digital, program-controlled device while retaining its functions.

I claim:

1. A treatment device for covering a human or animal body or body part comprising an arrangement of small permanent magnetic plates positioned between two sheets of flexible material and held at a distance from each other by seams through said flexible material, said seams surrounding said magnetic plates, said treatment device further comprising an electromagnetic field coil which is connected to a low-frequency variable current generator, the variable current of said generator producing a changing low-frequency magnetic field in said electromagnetic field coil, wherein, said changing low-frequency magnetic field produces corresponding movement in said small permanent magnetic plates proximate to said electromagnetic field coil.

2. A treatment device in accordance with claim 1, wherein said small permanent magnetic plates are polarized at longitudinal sides of said plates.

3. A treatment device in accordance with claim 2, wherein all said small permanent magnetic plates are polarized parallel oriented to each other.

4. A treatment device in accordance with claim 1, wherein said small permanent magnetic plates are of rectangular shape and said two sheets of flexible material are made from a fabric.

5. A treatment device in accordance with claim 4, wherein an elastic material is inserted in a distance between said small permanent magnetic plates.

6. A treatment device in accordance with claim 5, wherein said two sheets of flexible material covering said small magnetic plates are rectangular shaped.

7. A treatment device in accordance with claim 1, wherein straps are attached to said two sheets of flexible material covering said small permanent magnetic plates to assist in wrapping said flexible material covering on said body part.

8. A treatment device in accordance with claim 1, wherein said low frequency variable current generator has a first oscillator with a frequency control means for operating said oscillator within a range of 0.5 to 30 Hz, said oscillator connected via a first switch contact to a sniusoidal alternating voltage source of a line frequency of 60 Hz, and via a second switch contact to a semi-sinusoidal variable voltage source of line frequency of 60 Hz.

9. A treatment device in accordance with claim 8, wherein an alternating voltage is provided to a triac, wherein a control input of said triac is driven by said first oscillator and the output of said triac is fed to a control transformer the output of which is routed via said first switch contact directly to an output connector of said low frequency current generator, and wherein the output of said control transformer is routed via said second switch contact and further via a rectifier diode to said output connector of said low frequency current generator.

10. A treatment device in accordance with claim 8, wherein said low frequency generator comprises a second oscillator supplying rectangular voltage pulses with a pre-determinable frequency of 1 to 1,000 Hz, said second oscillator controlling a rectangular voltage pulse generator provided with setting means for an output voltage amplitude.

11. A treatment device in accordance with claim 10, wherein said second oscillator output is coupled to a square wave generator providing complimentary output signals which are fed to corresponding control inputs of two groups of switches which are supplied by line voltage delivered by a step down transformer via a rectifier, and wherein the outputs of the two groups of switches are connected to corresponding output connectors of said low frequency current generator.

12. A treatment device in accordance with claim 1, further comprising switch means for selectively operating said first oscillator and said second oscillator.

13. A treatment device in accordance with claim 1, wherein a frame supports a pallet having a space for said body to be treated, wherein said electromagnetic field coil surrounds said pallet with an upper part of said field coil covering said space and said small permanent magnetic plates and wherein said field coil is disposed in and surrounded by a coil channel which is composed of an upper and a lower channel section, wherein said upper and said lower channel are connected to each other with pivot joints.

14. A treatment device in accordance with claim 1, wherein a frame supports a pallet having a space for said body to be treated, wherein said field coil surrounds said pallet, an upper part of said field coil covering, said space and said small permanent magnetic plates, wherein said field coil comprises a plurality of field coils which are spaced and movable along the longitudinal axis of said frame and are arranged coaxially to each other.

15. A treatment device in accordance with claim 14, wherein said frame is mounted on rollers.

16. A treatment device in accordance with claim 14, wherein said small permanent magnetic plates positioned between said two sheets of flexible material are located on said pallet.

17. A treatment device in accordance with claim 14, wherein said field coils are each connected with an associated controllable pulse generator switch, each said pulse generator switch controlled via a state control switch, first switch contacts on said state control switch connecting said pulse generator switch synchronously to an oscillator provided with a frequency control, second switch contacts on said state control switch connecting said pulse generator switch via a phase-shifter to said oscillator, third switch contacts on said state control switch connecting said pulse generator switch individually to said oscillator each of which is provided with a frequency control, wherein said phase-shifter generates a phase shift sequence progressing from each said pulse generator switch to the next in turn.

* * * * *